(12) United States Patent
Vasek et al.

(10) Patent No.: US 6,415,823 B1
(45) Date of Patent: Jul. 9, 2002

(54) CATHETER TIP INSERT

(75) Inventors: Jeffrey A. Vasek, Santa Barbara; Lori Cone Speckman, Ventura, both of CA (US)

(73) Assignee: Medtronic, INC, Minneapolis, MN (US)

( * ) Notice: Subject to any disclaimer, the term of this patent is extended or adjusted under 35 U.S.C. 154(b) by 0 days.

(21) Appl. No.: 09/302,605

(22) Filed: Apr. 30, 1999

(51) Int. Cl.7 .............................................. B65O 59/00
(52) U.S. Cl. ...................... 138/96 R; 138/89; 604/256
(58) Field of Search .................. 138/96 R, 89, 138/89.1–89.4; 604/256

(56) References Cited

U.S. PATENT DOCUMENTS

| | | | | |
|---|---|---|---|---|
| 3,307,552 A | * | 3/1967 | Strawn | 138/96 R |
| 3,589,368 A | * | 6/1971 | Jackson | 138/96 R |
| 3,835,862 A | * | 9/1974 | Villari | 138/96 R |
| 5,280,809 A | * | 1/1994 | Tive | 138/96 R |
| 5,443,081 A | * | 8/1995 | Klosterman | 128/772 |
| 5,738,666 A | | 4/1998 | Watson et al. | 604/264 |
| 5,996,637 A | * | 12/1999 | Larsson | 138/96 R |

OTHER PUBLICATIONS

Medtronic PS Medical Model 99102 "Innervision Catheter".

* cited by examiner

*Primary Examiner*—Patrick Brinson
(74) *Attorney, Agent, or Firm*—Curtis D. Kinghorn; Tom Berry

(57) ABSTRACT

An insert is disclosed that is placed in the slit in a slit tipped catheter during storage of the catheter. This insert prevents opposite of the slit from contacting and forming bonds that tend to close the slit. When the catheter is to be used, the insert is removed and the catheter is used in its intended way.

23 Claims, 5 Drawing Sheets

CATHETER TIP INSERT

BACKGROUND OF THE INVENTION

1. Field of the Invention

The invention relates to catheters used to drain cerebrospinal fluid from the ventricles of a brain and more particularly relates to a device for preventing the closure of such a catheter having a slit tip at the end of the shunt.

2. Description of Related Art

A typical adult has a total of about 120–150 cc of (cerebrospinal fluid) CSF with about 40 cc in the ventricles in the brain. A typical adult also produces about 500 cc/day of CSF, all of which is reabsorbed into the blood stream on a continuous basis. CSF is comprised primarily of water but also includes small amounts of minerals and proteins.

Hydrocephalus is a condition of excessive accumulation of CSF in the ventricles or brain cavities. Hydrocephalus can result from congenital conditions interfering with normal CSF circulation or as the result of a problem with CSF reabsorbtion.

Excessive accumulation of CSF, due to hydrocephalus causes increased pressure upon the brain. Whatever the cause, over time, this increased CSF pressure causes damage to the brain tissue. It has been found that shunting the excess CSF to another area of the body pressure is therapeutically beneficial and generally allows the patient to lead a full and active life.

To treat the condition of hydrocephalus a shunt is used as a conduit to transport CSF from one location in the body to another. A typical shunt for transporting CSF from the ventricle to another part of the body is comprised of a ventricular catheter, valve and distal catheter. CSF shunts also exist for transporting fluid from the spine to another part of the body.

A common material for shunt catheters is silicone. Examples of systems to continuously drain excess CSF from the ventricles of the brain are the Delta® Shunt and the CSF—Flow Control Shunt Assembly made and sold by Medtronic—PS Medical of Goleta, Calif. Such systems use a catheter 2 that is placed in the patient's ventricle 4 in the brain 6 (FIG. 14) to drain the excess CSF.

All of these systems continuously transport excess accumulation of CSF from the patient's ventricle through the catheter 2 to another part of the family. It has been shown to be highly advantageous to use fiber-optic technology to help place a ventricular catheter such as catheter 2 in the ventricles 4 of a brain 6. To this end, as shown in FIG. 5, endoscopes 8 have been developed that are passed through the central lumen 16 of the catheter 2. These endoscopes 8 are advanced beyond the ultimate ventricular end 10 of the catheter 2 once the catheter 2 has been placed in the ventricle 4 of the brain 6.

As the endoscope 8 is advanced beyond the ultimate ventricular end 10 of the catheter 2, the physician is able to view the environment of the ventricle 4 to determine whether the catheter 2 is placed at a desirable location. If the catheter 2 is not located at a desirable location, the physician can change the location of the catheter 2 and confirm, by viewing the location through the endoscope 8, that the final location of the ultimate ventricular end 10 of catheter 2 is a desired location.

In such a system incorporating both an endoscope 8 and a catheter 2, catheter 2 is preferably of the type disclosed in U.S. Pat. No. 5,738,666 issued to David A. Watson and Lori Cone Speckman on Apr. 14, 1998 entitled "Slit Tip Ventricular Catheter and Method of Manufacturing Same", the teaching of which is incorporated herein in its entirety by reference. Such a catheter is shown in FIGS. 1–6 generally labeled 2. Catheter 2 has a proximal end 12, a distal end 14 and a central lumen 16. A plurality of holes 18 are located at the distal end 14. A valve is attached proximal to the plurality of holes 18.

A slit 20 is located at the ultimate ventricular end 10. Slit 20 extends across the ultimate ventricular end 10. Slit 20 is defined by a first side wall 22 and a second side wall 24 that meet at contact points 26 and 28. First and second side walls 22, 24 each have a midpoint 30. When slit 20 is closed, first side wall 22 is in contact with second side wall 24 along substantially the entire length of both first and second side walls 22, 24. When slit 20 is open, first and second side walls 22, 24 are separated at their respective midpoints 30. Such a catheter 2 is the Model #99102 "Innervision Catheter" sold by Medtronic—PS Medical of Goleta, Calif.

In use, as shown in FIG. 2, when the distal end 34 of an endoscope 8 is passed through catheter 2, the distal end 34 will contact slit 20. As shown in FIG. 3, as distal end 34 is advanced distally, distal end 34 will pass through slit 20 and extend distally beyond the ultimate ventricular end 10 of catheter 2.

Catheter 2 is typically made. of silicone. During storage, slit 20 will be in the "closed" position so that first and second side walls 22, 24 will be in contact along substantially their entire lengths. A problem with this is that when silicone comes into contact with silicone for an extended time period, silicone to silicone bonds forms. This phenomenon is called "contact bonding". With catheter 2, when catheter 2 is in the "closed" position, contact bonding begins to occur between first and second side walls 22, 24. This tends to "close" slit 20 so that slit 20 will not easily "open" when needed as the distal end 34 of endoscope 8 is advanced through slit 20. This is a problem in need of a solution.

Although catheter 2 has been described as being made of silicone, the problem of the slit 20 closing due to bond formation may also occur in catheters made of any polymeric material susceptible to contact bonding. Examples of such polymeric material include, but are not limited to, natural and synthetic latex, plastized PVC, thermoplastic elastomers and polyurethanes as will be clear to those skilled in the art.

SUMMARY OF THE INVENTION

An insert is disclosed that is placed in the slit in a slit tipped catheter during storage and transport of the catheter. This insert prevents the opposite sides of the slit from contacting and forming bonds that tend to close the slit. When the catheter is to be used, the insert is removed and the catheter is used in its intended way.

It is therefore a primary object of the invention to provide a device that prevents the slit in a slit tipped catheter made of a material susceptible to contact bonding from closing due to bonds forming between opposite sides of the slit during storage and transport of the catheter.

It is another object of one embodiment of the invention to provide a device that prevents the slit in a slit tipped catheter made of a material susceptible to contact bonding from closing due to bonds forming between opposite sides of the slit during storage and transport of the catheter that will not adversely affect the ultimate operation of the catheter.

These and other objects of the invention will be clear from the description of the invention given herein and particularly with reference to the attached drawings and the Detailed Description of the Invention. Throughout this description, like reference numbers refer to like elements.

DETAILED DESCRIPTION OF THE INVENTION

Figure 1:
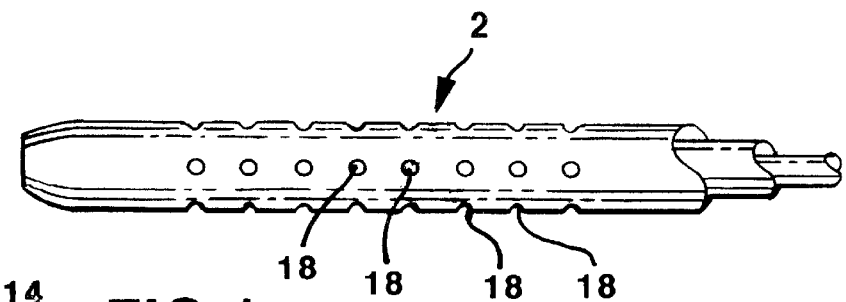
FIG. 1 is a side view of a slit tip catheter.
Figure 2:
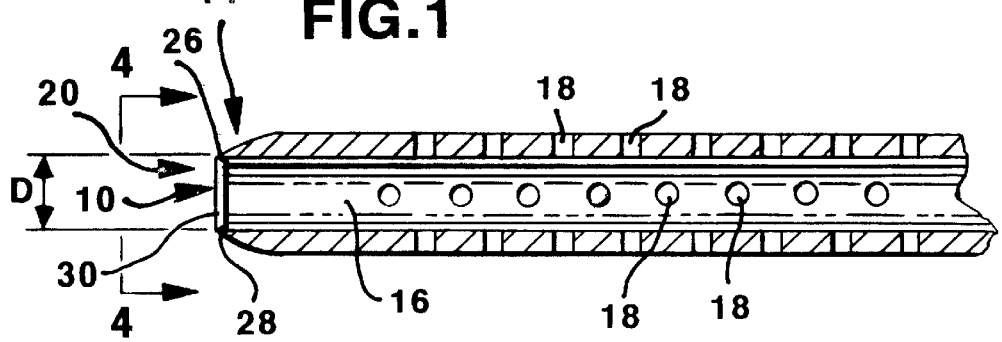
FIG. 2 is a side cross-sectional view of the catheter of FIG. 1.
Figure 3:
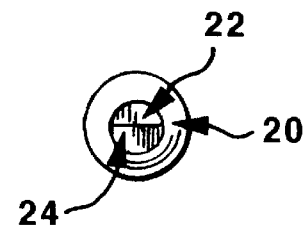
FIG. 3 is an end view of the catheter of FIG. 1.
Figure 4:
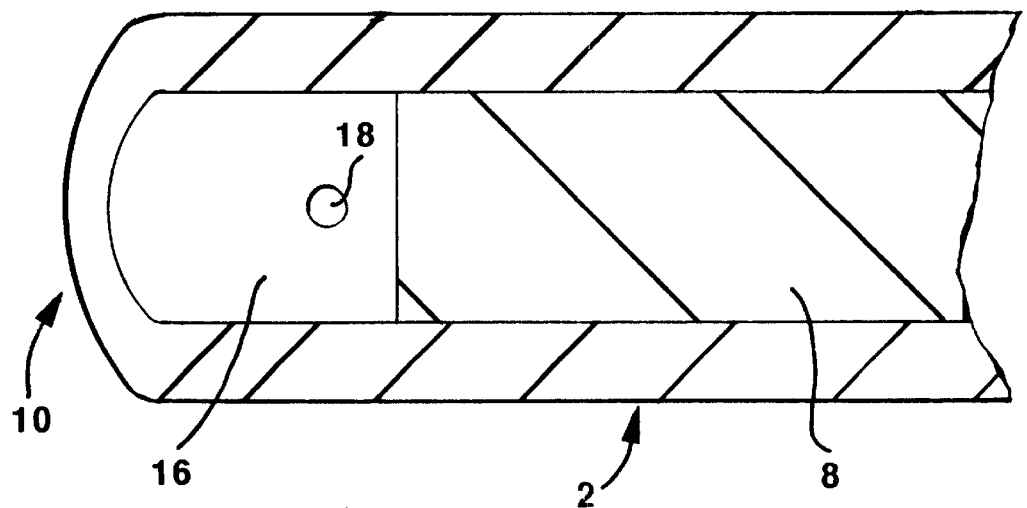
FIG. 4 is a side cross-sectional view of the catheter of FIG. 1 and an endoscope being advanced through the catheter.
Figure 5:
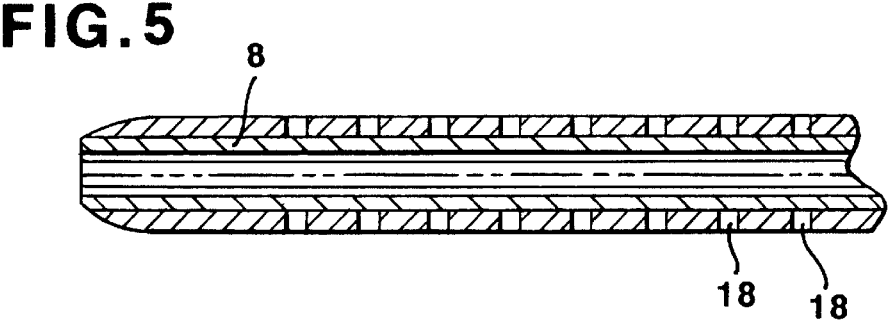
FIG. 5 is a side cross-sectional view of the catheter of FIG. 1 and an endoscope with the endoscope at the distal end of the catheter.
Figure 6:
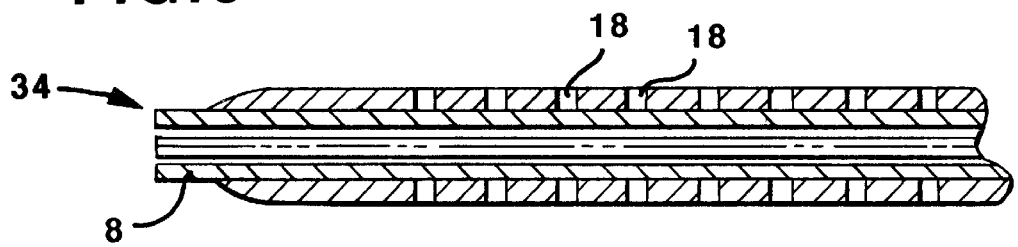
FIG. 6 is a side cross-sectional view of the catheter of FIG. 1 with the endoscope in use to place the catheter in the ventricles of a brain.
Figure 7:
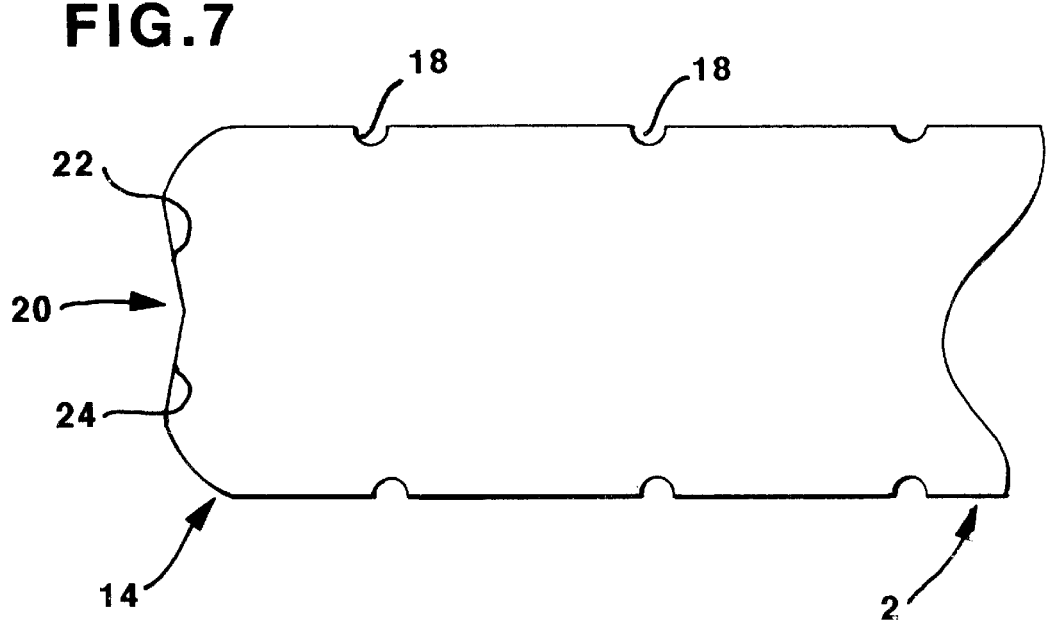
FIG. 7 is a top view of the catheter of FIG. 1 in an "open" position.
Figure 8:
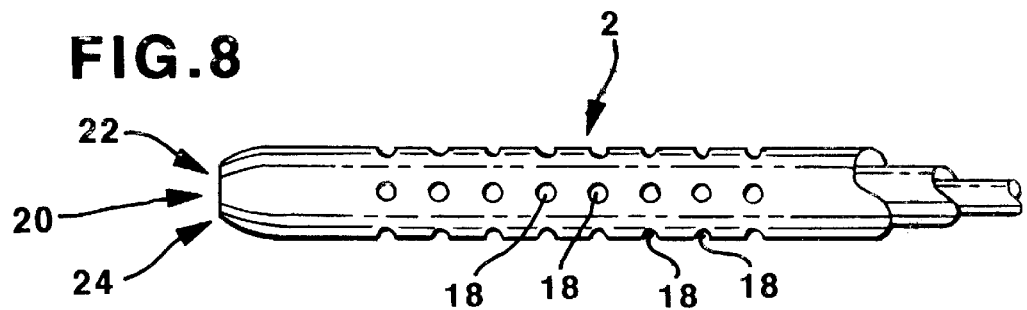
FIG. 8 is a top view of the catheter of FIG. 1 in an "closed" position.
Figure 9:
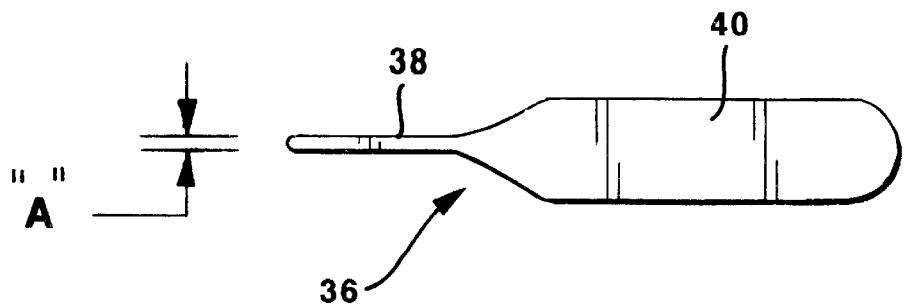
FIG. 9 is a side view of the present invention.

Referring to FIGS. 9 and 16, the invention, shown generally labeled 36, consists of an insert. Insert 36 has a lumen portion 38 and a grip portion 40.

In use, as will be described hereafter, lumen portion 38 will extend into lumen 16 of catheter 2 through slit 20. As a result, lumen portion 38 is preferably sized to have a height "A" about equal to the diameter "D" of the lumen 16 of catheter 2. In this way, when insert 36 is in place within catheter 2, lumen portion 38 will prevent first and second side walls 22, 24 from contacting each other and forming contact bonds between each other.

Figure 10:
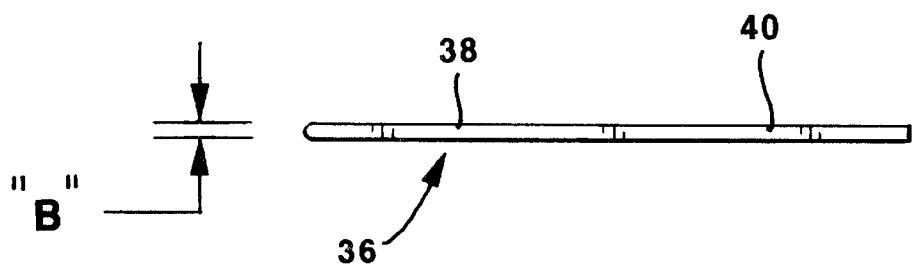
FIG. 10 is a top view of the preferred embodiment of the present invention.

As can be seen in FIG. 10, insert 36 is preferably narrow at both lumen portion 38 and grip portion 40, having a width "B" as small as possible but in any case less than the diameter "D" of the lumen 16 of catheter 2. Insert 36 is preferably as narrow as possible so that slit 20 will form as close to a closed configuration as possible with lumen portion 38 in place in lumen 16 through slit 20. In this way, during storage and transport of the catheter 2, as little undesirable stress as possible is applied to slit 20 so that, when used, catheter 2 is most likely to perform as desired.

For example, catheter 2 may have a central lumen with a diameter "D" of about 0.050". In the preferred embodiment, the height "A" of lumen portion 38 would then be about 0.045". As mentioned, the width "B" of lumen portion 38 should be as small as possible. Using currently available materials, the width "B" is preferably about 0.005–0.006". The previous specific dimensions are given as an illustration of the invention and are not intended to limit the scope of the invention.

The preferred way to make this embodiment of insert 36 is to cut out or stamp out insert 36 from a single sheet of material having a thickness equal to width "B". Alternately, insert 36 could be molded in one piece from the desired material as explained above.

Figure 11:
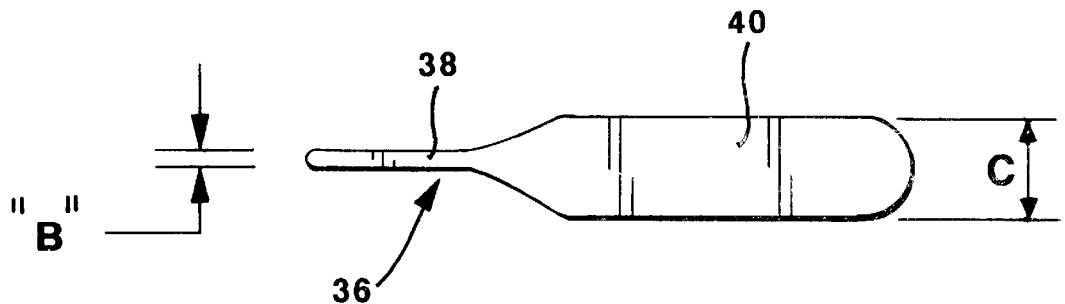
FIG. 11 is a top view of an alternate embodiment of the present invention.

In an alternate embodiment shown in FIG. 11, lumen portion 38 has the height "A" described above but grip portion 40 has a width "C" larger than width "B". In this embodiment, the increased width of grip portion 40 may make it easier to grasp grip portion 40 since there is more material to grip. But, a disadvantage of this embodiment is that more material and a more complex manufacturing process is required to produce this embodiment than is needed to produce the preferred embodiment. In this embodiment, insert 36 may be molded in one piece or lumen portion 38 and grip portion 40 may be made separately and joined together using well known joining techniques.

Both the lumen portion 38 and the grip portion 40 of insert 36 are preferably made of a material that is immune to contact bonding with the material of first and second side walls 22, 24. The preferred material of insert 36 is a spunbonded HDPE (High Density Polyethylene) that is sold under the brand name "Tyvek" by E. I. du Pont de Nemours and Company of Wilmington, Del. Although spunbonded HDPE is the preferred material of insert 36, other material can be used as well so long as the material serves the key function of serving as a barrier between the first and second side walls 22, 24 of slit 20. Examples of such alternate material include, but are not limited to, polyolefins, plastics, paper, ceramic and cellulose.

Although the preferred embodiment has both the lumen portion 38 and the grip portion 40 being made of a material that serves as a barrier between the first and second side walls 22, 24 of slit 20, it is within the scope of an alternate embodiment to have only the lumen portion 38 made of such a material and to have the grip portion 40 made of any other material. Of course, in this embodiment the material of grip portion 40 should allow grip portion 40 to be gripped and should allow grip portion 40 to be connected to lumen portion 38. Grip portion 40 can be connected to lumen portion 38 through adhesives, mechanical, chemical or other means as will be clear to those skilled in the art. In addition, grip portion 40, in any embodiment, may have ridges, grooves, bumps or other surface modifications 42 to allow better gripping of grip portion 40 as will be clear to those skilled in the art.

Figure 12:
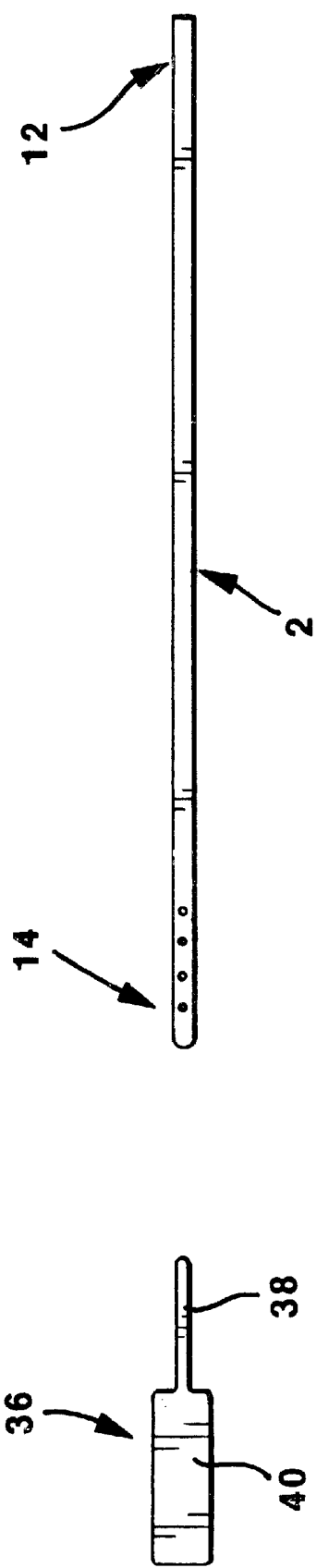
FIG. 12 is a side view of the slit tip catheter of FIG. 1 and the present invention aligned for insertion of the invention into the slit tip catheter.
Figure 13:
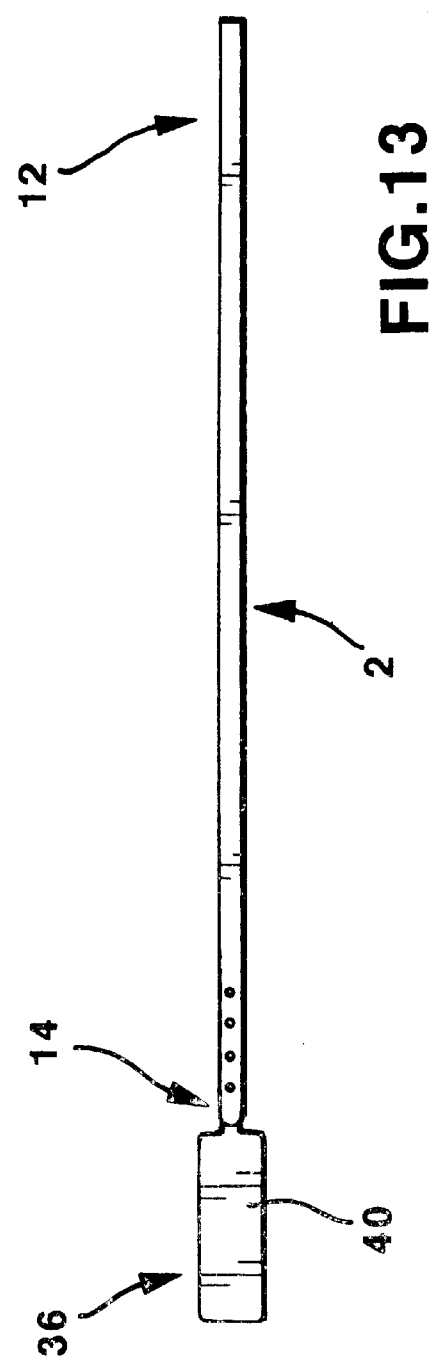
FIG. 13 is a side view of the slit tip catheter of FIG. 1 and the present invention with the invention inserted into the slit tip catheter.
Figure 14:
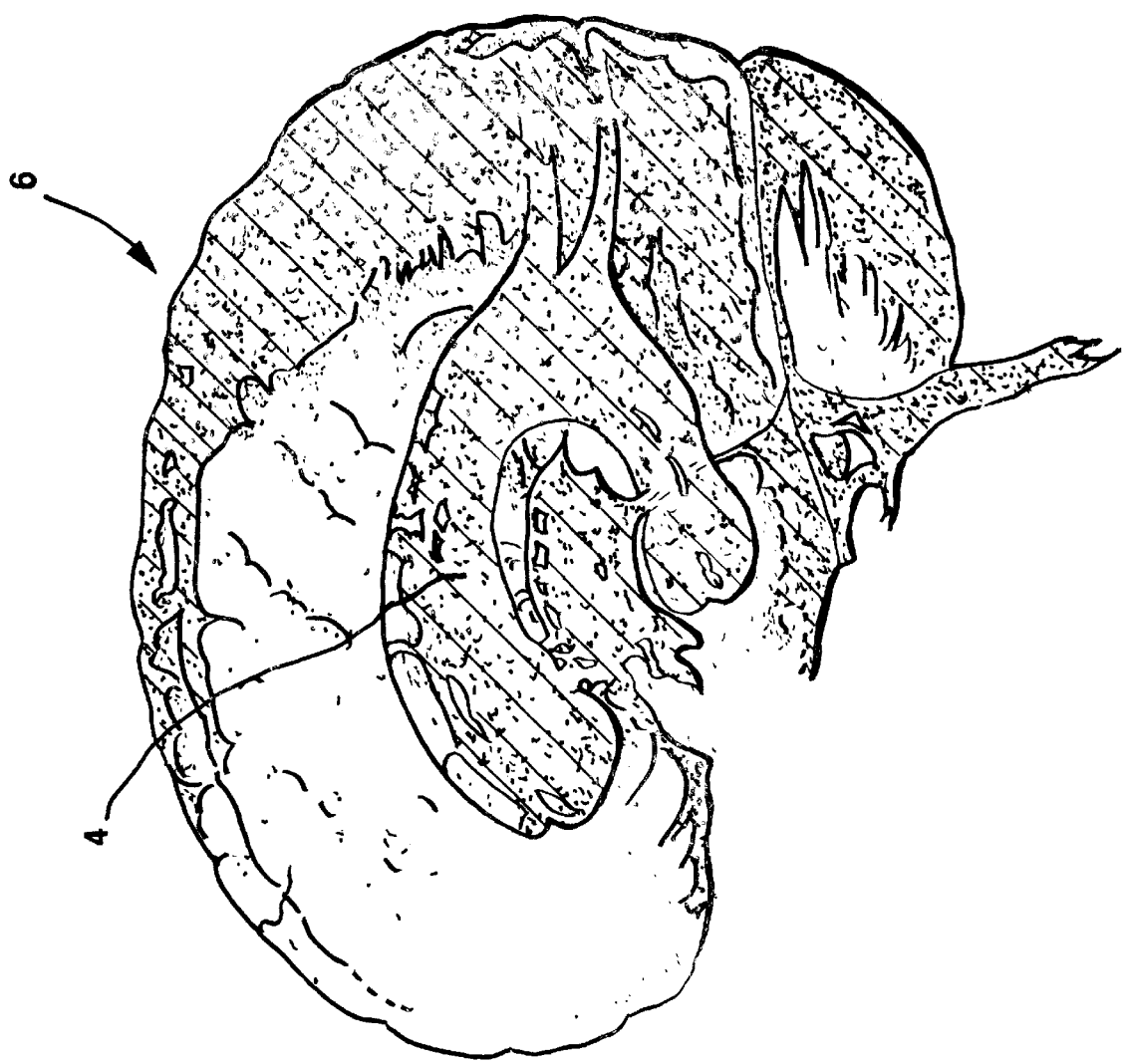
FIG. 14 is a perspective view of a human brain with the ventricles shown in phantom.

In use, lumen portion 38 of insert 36 is aligned with slit 20 as shown in FIG. 12. Lumen portion 38 is then passed through slit 20 into lumen 16 of catheter 2 so that the plane of lumen portion 38 is aligned with the plane of slit 20 (FIG. 13). In this way, first and second side walls 22, 24 contact opposite sides of lumen portion 38 and are thus prevented from contacting each other along their entire lengths. Because lumen portion 38 is made of a material resistant to bonding with the material of first and second side walls 22, 24, no bonds will be formed between first and second side walls 22, 24 and the material of lumen portion 38.

When it is desired to use catheter 2, the clinician will grasp the grip portion 40 of insert 36 and gradually pull the lumen portion 38 from lumen 16 of catheter 2. When lumen portion 38 is clear of slit 20, first and second side walls 22, 24 will come into contact with each other and form the intended seal at the ultimate ventricular end 10 of catheter 2. The insert 36 may be discarded as is appropriate. When the distal end 34 of endoscope 8 is advanced to slit 20, the distal end 34 will pass through slit 20 beyond the ultimate ventricular end 10 of catheter 2 to allow the physician to verify placement of the catheter 2 at the desired location in the ventricle 4 of the brain 6.

The description contained herein is intended to be illustrative and not exhaustive. Many variations and alternatives will occur to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. An insert for use with a catheter having a distal end and a central lumen with a central lumen diameter, the distal end having a slit that closes the distal end, the slit defined by opposed side walls that contact each other in an unstressed condition to close the distal end of the catheter and that are capable of moving apart from each other to open the distal end of the catheter, the insert comprising:

a flat lumen portion sized to be insertable into the central lumen through the slit, the lumen portion having a height and a width; and, a grip portion connected to the lumen portion.

2. The insert of claim 1, wherein the lumen portion has a height about equal to the diameter of the central lumen.

3. The insert of claim 1 wherein the width of the lumen portion is less than the diameter of the central lumen.

4. The insert of claim 3 wherein the width of the lumen portion is substantially less than the diameter of the central lumen.

5. The insert of claim 3 wherein the width of the lumen portion is about 10% of the diameter of the central lumen.

6. The insert of claim 1 wherein the grip portion has surface modifications to enhance the gripping of the grip portion.

7. The insert of claim 1 wherein the lumen portion is made of a material that is immune to contact bonding with the material of the opposed side walls of the slit.

8. The insert of claim 7 wherein the material is a spunbonded HDPE.

9. The insert of claim 7 wherein the material is chosen from the group consisting of polyolefins, plastics, paper, ceramic and cellulose.

10. The insert of claim 1 wherein the lumen portion and the grip portion are made of the same material.

11. The insert of claim 10 wherein the material of the lumen portion and the grip portion is a material that is immune to contact bonding with the material of the opposed side walls of the slit.

12. The insert of claim 11 wherein the material is a spunbonded HDPE.

13. The insert of claim 11 wherein the material is chosen from the group consisting of polyolefins, plastics, paper, ceramic and cellulose.

14. The insert of claim 1 wherein the lumen portion and the grip portion are made in one piece of the same material.

15. The insert of claim 14 wherein the material of the lumen portion and the grip portion is a material that is immune to contact bonding with the material of the opposed side walls of the slit.

16. The insert of claim 15 wherein the material is a spunbonded HDPE.

17. The insert of claim 15 wherein the material is chosen from the group consisting of polyolefins, plastics, paper, ceramic and cellulose.

18. The insert of claim 1 wherein the lumen portion and the grip portion are made separately and joined together to form the insert.

19. A method of using an insert with a catheter, the catheter having a distal end and a central lumen with a central lumen diameter, the distal end having a slit that closes the distal end, the slit defined by opposed side walls that contact each other in an unstressed condition to close the distal end of the catheter and that are capable of moving apart from each other to open the distal end of the catheter, the insert having a flat lumen portion sized to be insertable into the central lumen through the slit, the lumen portion having a height and a width, and a grip portion connected to the lumen portion, the method comprising the steps of:

passing the lumen portion through the slit into the lumen of the catheter;

retaining the lumen portion between the opposed side walls of the slit until the catheter is to be used; and removing the lumen portion from the catheter.

20. An insert for use with a catheter having a distal end and a central lumen with a central lumen diameter, the distal end having a slit that closes the distal end, the slit defined by opposed side walls that contact each other in an unstressed condition to close the distal end of the catheter and that are capable of moving apart from each other to open the distal end of the catheter, the insert comprising:

a lumen portion sized to be insertable into the central lumen through the slit, the lumen portion having a height and a width, wherein the lumen portion is made of a material that is immune to contact bonding with the material of the opposed side walls of the slit and wherein the material is a spunbonded HDPE; and, a grip portion connected to the lumen portion.

21. An insert for use with a catheter having a distal end and a central lumen with a central lumen diameter, the distal end having a slit that closes the distal end, the slit defined by opposed side walls that contact each other in an unstressed condition to close the distal end of the catheter and that are capable of moving apart from each other to open the distal end of the catheter, the insert comprising:

a lumen portion sized to be insertable into the central lumen through the slit, the lumen portion having a height and a width; and, a grip portion connected to the lumen portion;

wherein the lumen portion and the grip portion are made of the same material;

wherein the material of the lumen portion and the grip portion is a material that is immune to contact bonding with the material of the opposed side walls of the slit; and wherein the material is a spunbonded HDPE.

22. An insert for use with a catheter having a distal end and a central lumen with a central lumen diameter, the distal end having a slit that closes the distal end, the slit defined by opposed side walls that contact each other in an unstressed condition to close the distal end of the catheter and that are capable of moving apart from each other to open the distal end of the catheter, the insert comprising:

a lumen portion sized to be insertable into the central lumen through the slit, the lumen portion having a height and a width; and, a grip portion connected to the lumen portion;

wherein the lumen portion and the grip portion are made in one piece of the same material;

wherein the material of the lumen portion and the grip portion is a material that is immune to contact bonding with the material of the opposed side walls of the slit; and wherein the material is a spunbonded HDPE.

23. An insert for use with a catheter having a distal end and a central lumen with a central lumen diameter, the distal end having a slit that closes the distal end, the slit defined by opposed side walls that contact each other in an unstressed condition to close the distal end of the catheter and that are capable of moving apart from each other to open the distal end of the catheter, the insert comprising:

a lumen portion sized to be insertable into the central lumen through the slit, the lumen portion having a height and a width; and, a grip portion connected to the lumen portion; and wherein the lumen portion and the grip portion are made separately and joined together to form the insert.

* * * * *

UNITED STATES PATENT AND TRADEMARK OFFICE
CERTIFICATE OF CORRECTION

PATENT NO. : 6,415,823 B1
DATED : July 9, 2002
INVENTOR(S) : Jeffrey A. Vasek and Lori Cone Speckman It is certified that error appears in the above-identified patent and that said Letters Patent is hereby corrected as shown below:

Title page,
Item [57], ABSTRACT,
Lines 3-4, reads "..prevents opposite of the slit from…" should read -- …prevents opposite sides of the slit from… --

Signed and Sealed this

Fifth Day of April, 2005

JON W. DUDAS
*Director of the United States Patent and Trademark Office*